United States Patent
Ohnishi et al.

(10) Patent No.: US 8,012,680 B2
(45) Date of Patent: Sep. 6, 2011

(54) MICROCHIP, NUCLEIC ACID EXTRACTING KIT, AND NUCLEIC ACID EXTRACTING METHOD

(75) Inventors: Michihiro Ohnishi, Kanagawa (JP); Keisuke Morishima, Kanagawa (JP); Takehiko Kitamori, Tokyo (JP)

(73) Assignee: Sony Corporation (JP)

( * ) Notice: Subject to any disclaimer, the term of this patent is extended or adjusted under 35 U.S.C. 154(b) by 239 days.

(21) Appl. No.: 10/550,302

(22) PCT Filed: Mar. 24, 2004

(86) PCT No.: PCT/JP2004/003998
§ 371 (c)(1), (2), (4) Date: Sep. 22, 2005

(87) PCT Pub. No.: WO2004/086055
PCT Pub. Date: Oct. 7, 2004

(65) Prior Publication Data
US 2006/0234241 A1   Oct. 19, 2006

(30) Foreign Application Priority Data
Mar. 24, 2003  (JP) ................ 2003-081605

(51) Int. Cl.
C12M 1/00 (2006.01)
C12Q 1/68 (2006.01)
C07H 21/04 (2006.01)
G01N 15/06 (2006.01)

(52) U.S. Cl. ..... 435/6; 435/283.1; 435/286.5; 422/68.1; 422/101; 422/120; 536/23.1

(58) Field of Classification Search ............... None
See application file for complete search history.

(56) References Cited

U.S. PATENT DOCUMENTS 4,015,031 A * 3/1977 Reinhardt et al. ............ 427/213
5,587,128 A * 12/1996 Wilding et al. .............. 422/50

(Continued)

FOREIGN PATENT DOCUMENTS

JP   08-24600   1/1996

(Continued)

OTHER PUBLICATIONS

Sato et al "Microchip-based immunoassay system with branchingmultichannels for simultaneous determination of interferon-gamma" Electrophoresis, 2002, 23: 734-739.*

Kiichi Sato et al. "Integration of Chemical and Biochemical Analysis Systems into a Glass Microchip", Analytical Sciences, Jan. 2003, pp. 15-22, vol. 19, No. 1, The Japan Society for Analytical Chemistry.

J. Kim et al., "A Disposable Passive Microfluidic System Integrated With Micromixer and DNA Purification Chip for DNA Sample Preparation", (2002) Proceedings of the micro TAS 2002 symposium, Nara, pp. 224-226.

(Continued)

Primary Examiner — Betty Forman
(74) Attorney, Agent, or Firm — Finnegan, Henderson, Farabow, Garrett & Dunner, LLP (57) ABSTRACT

A new technical means is provided that can be produced and prepared at low cost, and in which the generation of stagnation in the flow of a liquid sample can be suppressed, microbeads can be smoothly and simply injected, filled and transported and the generation of dust can be also suppressed and a new extracting method for nucleic acid using the new technical means is provided. A microchip has a microchannel (3) formed by groove parts (11, 21) provided in connecting surfaces of upper and lower substrates (1, 2). In the microchannel (3), a gap part (31) in which the section of the channel is reduced is provided in a central part upward and downward, rightward and leftward, or upward and downward and rightward and leftward the section thereof, and microbeads are checked.

11 Claims, 5 Drawing Sheets

U.S. PATENT DOCUMENTS

| | | | |
|---|---|---|---|
| 5,726,026 A | | 3/1998 | Wilding et al. |
| 5,900,481 A | * | 5/1999 | Lough et al. ............... 506/30 |
| 5,928,880 A | | 7/1999 | Wilding et al. |
| 6,184,029 B1 | | 2/2001 | Wilding et al. |
| 6,270,970 B1 | * | 8/2001 | Smith et al. ............... 435/6 |
| 6,272,939 B1 | * | 8/2001 | Frye et al. ............... 73/864.81 |
| 6,319,469 B1 | | 11/2001 | Mian et al. |
| 6,743,516 B2 | * | 6/2004 | Murphy et al. ............ 428/447 |
| 7,060,171 B1 | * | 6/2006 | Nikiforov et al. ........... 204/452 |
| 7,294,503 B2 | * | 11/2007 | Quake et al. ............ 435/288.5 |
| 2001/0055812 A1 | | 12/2001 | Mian et al. |
| 2004/0011650 A1 | * | 1/2004 | Zenhausern et al. ........ 204/547 |

FOREIGN PATENT DOCUMENTS

| | | | |
|---|---|---|---|
| JP | 3220158 | | 8/2001 |
| JP | 2002-503331 | | 1/2002 |
| JP | 2002-532715 | | 10/2002 |
| WO | WO 96/14934 A1 | | 5/1996 |
| WO | WO 00/36407 | | 6/2000 |
| WO | WO 01/32930 | | 5/2001 |
| WO | WO 01/38865 | | 5/2001 |
| WO | WO 0240874 | * | 5/2002 |

OTHER PUBLICATIONS

L. Ceriotti et al.., "Combined Nucleic Acid Extraction and Enrichment in Bead-Packed Plastic Beds", (2002) Proceedings of the micro TAS 2002 symposium, Nara, pp. 175-177.

Q. Wu et al., "Monolithic Sol-gel Microchip Device for Efficient Isolation of Nucleic Acid from Clinical Samples", (2002) Proceedings of the micro TAS 2002 symposium, Nara, pp. 198-200.

Darwin R. Reyes et al., "Micro total analysis systems. 1. Introduction, theory, and technology," Anal. Chem., vol. 74, No. 12 (2002) pp. 2623-2636.

English translation of the first Office Action issued from the State Intellectual Property Office of the People's Republic of China on May 9, 2008 in related Chinese Patent Application No. 200480008284.3, 2 of 5 pages provided.

Kiichi Sato et al., "Integration of Chemical and Biochemical Analysis Systems into a Glass Microchip," Anal. Sciences., vol. 19, (Jan. 2003) pp. 15-22.

* cited by examiner

MICROCHIP, NUCLEIC ACID EXTRACTING KIT, AND NUCLEIC ACID EXTRACTING METHOD

TECHNICAL FIELD

The present invention relates to a microchip, a kit for extracting nucleic acid and an extracting method for nucleic acid.

This application claims a priority based on Japanese Patent Application No. 2003-081605 filed on Mar. 24, 2003 in Japan, which is applied to this application by referring thereto.

BACKGROUND ART

Usually, a microchip technique has been known that grooves of a size having the depth of 100 μm and the width of about 500 μm or smaller are formed on the surface of a substrate such as glass by a microfabrication technique such as a lithography, the grooves are employed as microchannels for liquid or gas to enable a chemical reaction, a biochemical reaction, a solvent extraction, a gas-liquid separation and further a chemical analysis or a non-contact optical analysis of a slight amount of components based on them.

As for the microchip technique, the inventors of this application also propose a measure that microbeads as reaction carriers are inserted into microchannels and dam shaped check parts are provided in the microchannels (document 1).

With the recent progress of molecular genetics or molecular biology and the expansion of the application thereof to a medical care, it has been a very important problem to extract nucleic acid from a liquid sample. Accordingly, the use of the microchip technique has been studied to extract the nucleic acid. A method using silica beads, a method using silica micropillars or a method using a silica film has been hitherto proposed (documents 2 to 4).

However, in the usual microchip technique, the method for extracting the nucleic acid by using, for instance, the silica micropillars or the silica filter undesirably has a basic problem that a cost is high and when the silica micropillars or the silica filter are stained, they cannot be replaced by new micropillars or a new silica film. Further, in the existing method using the microbeads such as silica, high pressure has been necessary to inject the microbeads into the microchannels. Thus, the microchannels have not been easily filled with the beads.

In the usual method for checking the microbeads by the dam shaped check parts, stagnation is liable to arise in the flow of the liquid sample so that the microbeads such as silica are inconveniently hardly smoothly transported.

Further, usually, when the microchannels are formed by using glass or quartz as the substrate of the microchip, dust is apt to be generated in the channels and the dust may be undesirably hardly removed.

Related documents are shown below. These documents are applied to this application with reference thereto.

1: K. Sato et al., Anal. Chem. 72, 1144-1147 (2000)
2: L. Ceriotti et al., (2002) Proceedings of the micro TAS 2002 symposium Nara, pp. 175-177
3: J. Kim et. al., (2002) Proceedings of the micro TAS 2002 symposium, Nara, pp. 224-226
4: Q. Wu et al., (2002) Proceedings of the micro TAS 2002 symposium, Nara, pp. 198-200

DISCLOSURE OF THE INVENTION

Thus, in order to solve the above-described problems of the related art, it is an object of the present invention to provide a microchip of a new technique that can be produced and prepared at low cost as a microchip technique using microbeads that are not only effective for extracting nucleic acid, but also useful as various kinds of reaction carriers, and in which the generation of stagnation in the flow of a liquid sample can be suppressed, the microbeads can be smoothly and simply injected, filled and transported and the generation of dust can be also suppressed, and a new extracting method for nucleic acid using the microchip.

To achieve the above-described object, a microchip according to the present invention has a microchannel formed by groove parts provided in connecting surfaces of upper and lower substrates. The microchannel is provided with a gap part in which the section of the channel is reduced in a central part upward and downward, rightward and leftward, or upward and downward and rightward and leftward the section thereof. The gap part may be formed by protruding parts in the groove parts. Further, the gap part may be formed by the opposed protruding parts in the groove parts provided respectively in the upper and lower substrates. Further, the gap part may be formed by inserting the protruding part of one substrate into the groove part of the other substrate. Further, the size of the section of the gap part may be varied by at least one movable protruding part of the upper and lower substrates.

Still further, the size of the section of the gap part is a size necessary for checking microbeads inserted into the microchannel. The inner wall surface of the microchannel may be decorated with a surface treatment agent.

Still further, a kit for extracting nucleic acid according to the present invention includes: the above-described microchip and microbeads having surface hydroxyl groups. The microbeads having the surface hydroxyl groups are at least one kind of silica microbeads having a diameter of 10 μm or smaller, hollow silica microbeads, and resin microbeads. In the microchannel of the microchip having the surface hydroxyl groups on the inner wall surface, the surface hydroxyl groups may be coated with a surface treatment agent. The surface treatment agent is a silane coupling agent including trialkyl halogenosilane as a main component.

Further, an extracting method for nucleic acid uses the above-described kit for extracting nucleic acid. The nucleic acid in liquid to be processed is adsorbed on the surfaces of the microbeads in the microchannel of the microchip. Still further, the nucleic acid may be adsorbed on the surfaces of the microbeads under the existence of chaotropic ions.

BEST MODE FOR CARRYING OUT THE INVENTION

Now, an embodiment of a microchip, a kit for extracting nucleic acid and an extracting method for nucleic acid according to the present invention will be described by referring to the drawings.

Figure 1:
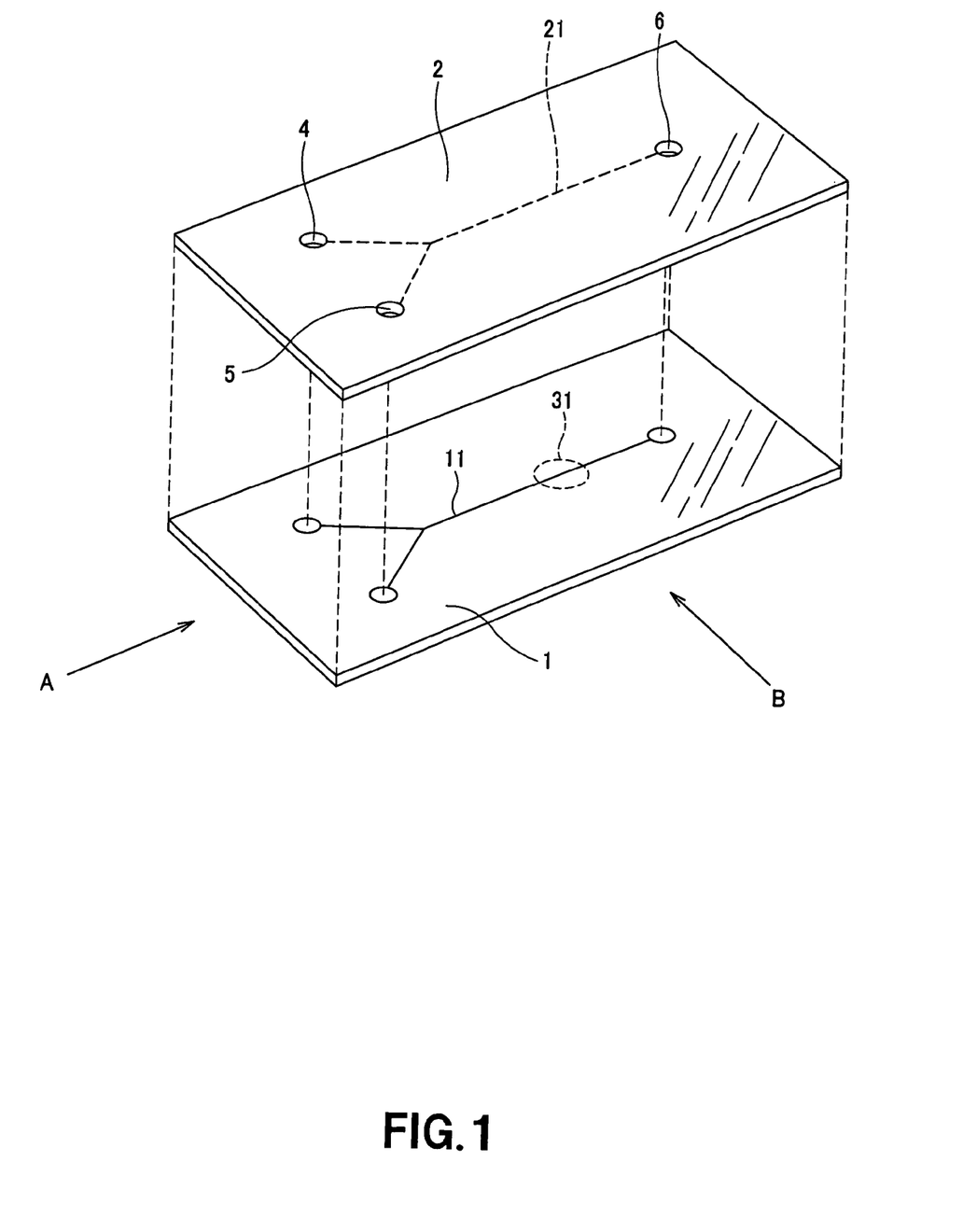
FIG. 1. is an exploded perspective view schematically showing a microchip.
Figure 2A:
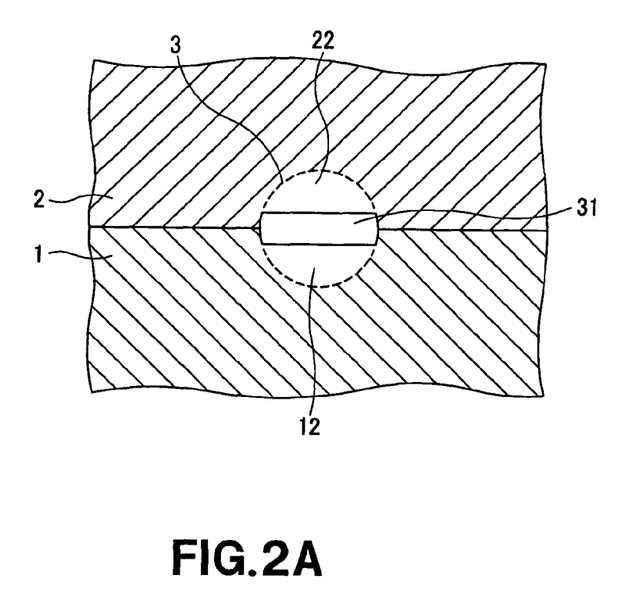
FIGS. 2A and 2B are sectional views of a gap part 31 viewed from directions A and B in FIG. 1.
Figure 2B:
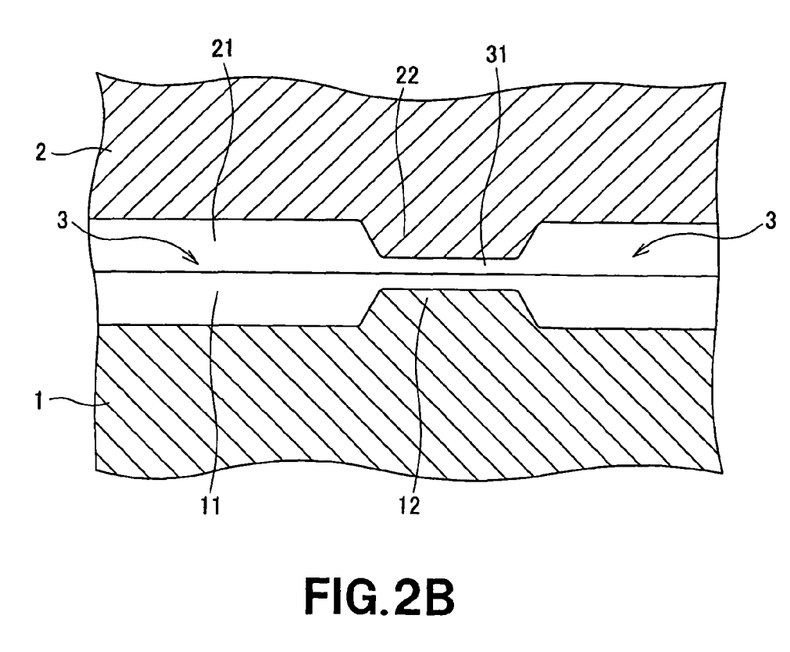

FIGS. 1 and 2 schematically show a partial structure of a microchip according to the present invention. FIG. 1 shows a state that a lower substrate 1 is separated from an upper substrate 2. FIG. 2 shows partial sections of a gap part 31, viewed from the directions of arrow marks A and B shown in FIG. 1, that is provided in a microchannel 3 under a state that the upper and lower substrates 1 and 2 are connected together For instance, in the microchip shown in FIGS. 1 and 2, the microchannel 3 is formed by groove parts 11 and 21 provided in the connecting surfaces of the upper and lower substrates 1 and 2. In the microchannel 3, the gap part 31 in which the section of the channel is reduced is provided in a central part upward and downward the section thereof.

More specifically, in the case of an example shown in FIGS. 1 and 2, the groove parts 11 and 21 of the upper and lower substrates 1 and 2 are opposed to each other to form the microchannel 3. Protruding parts 12 and 22 respectively provided in the groove parts 11 and 21 are opposed to each other to form the gap part 31.

Figure 3A:
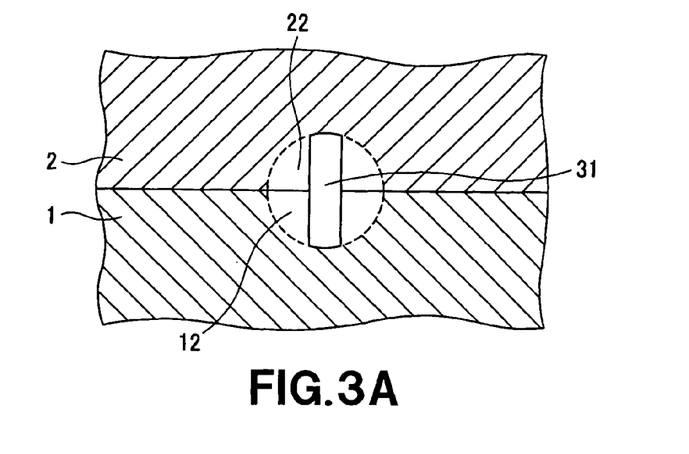
FIGS. 3A to 3C are sectional views showing other examples of the gap part 31.
Figure 3B:
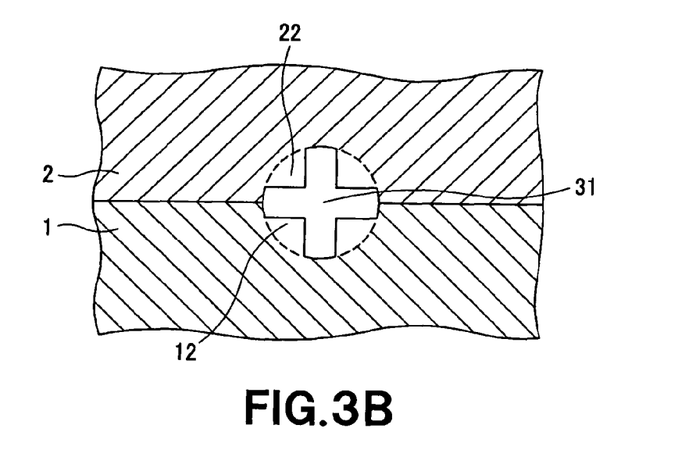
Figure 3C:
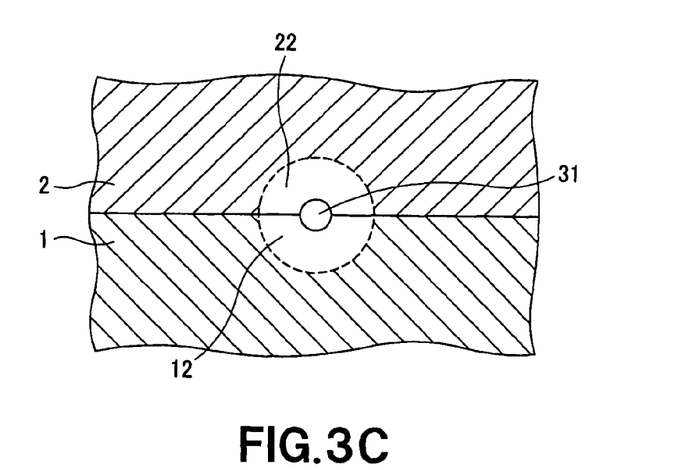

The gap part 31 may be located in the central part of the section of the microchannel 3. The gap part may be located not only in the central part upward and downward the section like a slit-shaped opening as illustrated in FIG. 2, but also in the central part rightward and leftward the section, as schematically shown in, for instance, FIG. 3A or in the central part upward and downward and rightward and leftward the section as shown in FIG. 3B. It is to be understood that the section of the gap part 31 may have various kinds of forms. For instance, as shown in FIG. 3C, the section of the gap part may have a circular form. These forms can be determined by considering a microfabrication means for forming the groove parts 11 and 21 and the protruding parts 12 and 22 of the microchip or conditions thereof, and the type or size of microbeads injected into the microchannel or the like.

Figure 4A:
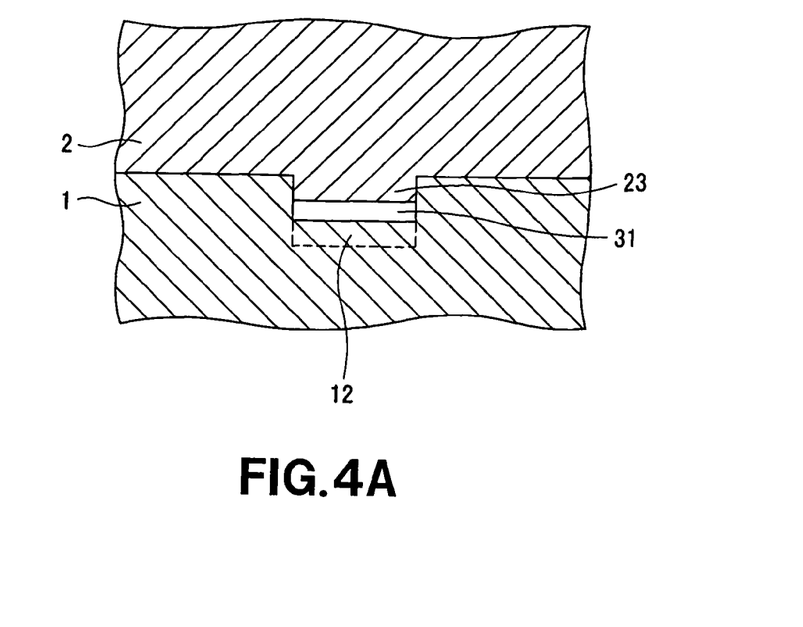
FIGS. 4A and 4B are sectional views showing an example of a still another gap part 31.
Figure 4B:
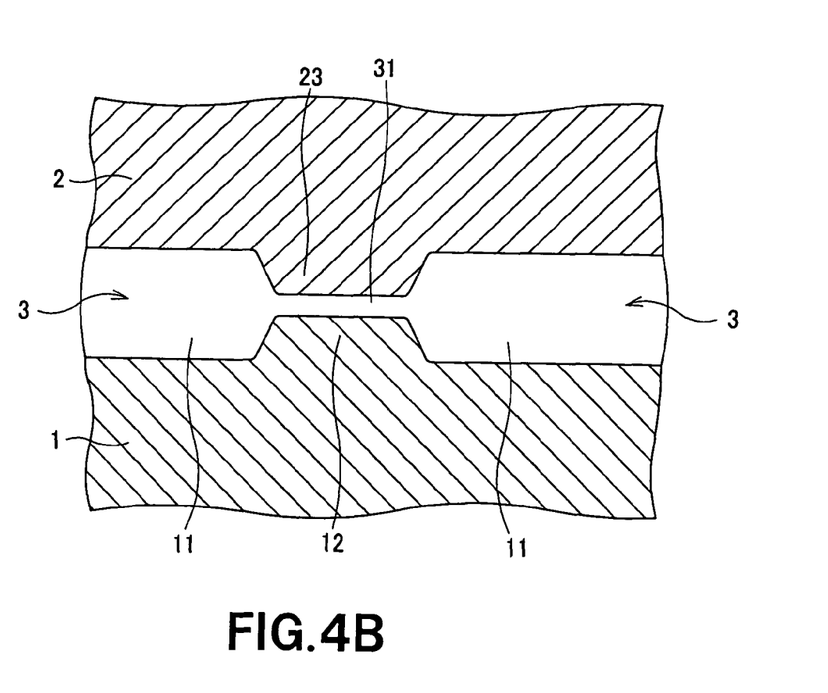

The gap part 31 may not be formed by the protruding parts 12 and 22 respectively provided in the groove parts 11 and 21 of the upper and lower substrates 1 and 2. For instance, as shown in FIG. 4, the microchannel 3 itself is formed by, for instance, the groove part 11 provided in the lower substrate 1. The upper substrate 2 is provided as a cover plate. In the structure of the microchannel 3, a protruding part 23 provided in the upper substrate 2 is inserted into the groove part 11. The protruding part 23 may be opposed to the protruding part 12 in the groove 11 to form the gap part 31.

It is to be understood that the gap part 31 may have various structures except the structures composed of the above-described protruding parts 12, 22 and 23.

Further, these protruding parts 12, 22 and 23 are not only formed by a microfabrication process by means of a lithographic etching of the substrates 1 and 2, but also formed by means of, for instance, curing a polymer. Further, the microchannel 3 may be externally operated by a micro-member or the microchannel 3 itself may be deformed to form the gap part 31.

In either case, in the microchip according to the present invention, the microchannel 3 or the gap part 31 can be produced and prepared simply and at low cost. Further, since the gap part 31 is provided in the central part of the section of the microchannel 3, when microbeads are injected into the microchannel 3, the generation of stagnation in the flow of fluid such as liquid or gas can be suppressed, the microbeads can be smoothly and simply injected and the microbeads can be also checked.

When the microbeads are used as described above, the gap part 31 provided in the microchannel 3 has such a size of the section as to check the microbeads injected into the microchannel 3. Further, for instance, a consideration is given to a case that the above-described protruding parts or members having the same functions as those of the protruding parts may be moved so that the size of the section of the gap part 31 may be varied. In the gap part 31 in which the size of the section is varied, after the microbeads in the microchannel 3 are checked, the section can be greatly increased so that the microbeads are moved to a downstream area. Ordinarily, to discharge the microbeads, the microbeads need to be discharged in the direction opposite to an injecting direction. However, in the gap part 31 whose section is variable, the microbeads can be discharged in a forward direction the same as the injecting direction.

For instance, in the microchip according to the present invention as described above, an inner wall surface may be decorated with a surface treatment agent depending on its purpose of use, the type or the property of an object so that a sample material, impurities, dust or the like do not adhere to the microchannel 3. For instance, in the case of the microchip made of glass or quartz, surface hydroxyl groups are ordinarily present on the surface of the inner wall of the microchannel 3. Thus, the surface hydroxyl groups may be possibly connected to nucleic acid so that a material such as the nucleic acid is hardly extracted and separated. In this case, the surface hydroxyl groups are effectively coated with the surface treatment agent to make the surface hydroxyl groups inactive. The microchip according to the present invention is combined with the microbeads to obtain an extremely useful kit for a characteristic chemical synthesis or analysis. Especially, in the present invention, as such a kit, a kit for extracting nucleic acid is provided that includes the above-described microchip and the microbeads having the surface hydroxyl groups.

As the microbeads having the surface hydroxyl groups in this case, silica microbeads that have a diameter of 10 μm or smaller, hollow silica microbeads, and beads made of a resin such as polystyrene having a surface to which hydroxyl groups are applied may be exemplified as preferable microbeads. The silica microbeads having the diameter of 10 μm or larger are hardly transported in the microchannel 3 depending on the level of its specific gravity.

Further, in the kit for extracting nucleic acid according to the present invention, the surface hydroxyl groups are preferably coated with a silane coupling agent for the inner wall surface of the microchannel having the surface hydroxyl groups.

Trialkyl halogenosilane having one halogen atom, that is, a silane coupling agent using a compound represented by a below-described general formula is most preferable.

General Formula:

Here, $R_1$, $R_2$ and $R_3$ in the formula represent the same or different alkyl groups. X represents a halogen atom such as a chlorine atom. In the case of a silane compound having two or more halogen atoms such as chlorine atoms, dust may be possibly produced due to not only the reaction of the halogen atoms as reaction groups with the hydroxyl groups on the surface of the inner wall, but also the polymerizing reaction of molecules. Accordingly, the use of the above-described silane compound is limited.

As an extracting method for nucleic acid, for instance, in the example of the microchip shown in FIGS. 1 and 2, liquid including the microbeads is injected from a liquid introducing port 4. In the microchannel 3, the liquid including the microbeads is checked in the gap part 31. Then, a sample is introduced from a liquid introducing port 5 to allow the microbeads to adsorb nucleic acid. Remaining liquid is discharged from a discharge port 6. The adsorption enables the nucleic acid to be extracted. The adsorbed nucleic acid can be desorbed from the microbeads by introducing desorbing liquid. Then, the nucleic acid is preferably extracted under the existence of chaotropic ions.

According to the present invention, the nucleic acid can be simply and highly efficiently extracted.

Now, Examples are shown below and more specifically described. It is to be understood that the present invention is not limited to the below-described Examples.

EXAMPLE 1

Transportation of Microbeads

A microchip made of glass was prepared (FIG. 1) that had a microchannel with the diameter of 50 μm and the length of 60 mm and including a check structure in a central part. A gap part was formed that had the dam shaped check structure by protruding parts both in an upper part and a lower part of the microchannel. The gap part in the central part of the microchannel was formed in a slit shape having a vertical length of 2 μm and a horizontal length of 50 μm. One port of the microchannel was used as an injecting port and the other port was used as a discharge port. A liquid reservoir was provided in the injecting port and a microtube was connected to the discharge port. An experimental system was assembled in which a syringe pump was connected to the microtube of the discharge port and liquid injected to the liquid reservoir could be sucked by the operation of the syringe pump and injected into the microchannel. Here, microbeads suspended in pure water were injected to the liquid reservoir and the transportation of the microbeads in the microchannel was observed by using an optical microscope. As the microbeads, silica microbeads (a diameter of 10 μm or smaller), silica microbeads (a diameter of 10 μm or larger), hollow silica microbeads (a diameter of 2 to 20 μm) and polystyrene microbeads having a surface to which hydroxyl groups were added (a diameter of 20 μm) were prepared. The liquid including the microbeads was sucked at a flow velocity of 10 μl per minute. All the microbeads except the silica microbeads (a diameter of 10 μm or larger) were satisfactorily transported in the microchannel and a column of the beads could be formed in a part immediately before the gap part of the check structure. On the other hand, when the same experiment was carried out by using the silica microbeads having the diameter of 10 μm or larger, a transportation is stopped halfway the microchannel so that the column was insufficiently formed. Particularly, the hollow silica microbeads and the polystyrene microbeads having the surface to which the hydroxyl groups were added were satisfactorily transported like silica nanobeads (beads having a diameter of 1 μm or smaller).

When the pure water was put into the liquid reservoir and injected to the microchannel, the microbeads except the silica microbeads (the diameter of 10 μm or larger) could be transported in the microchannel and discharged to the syringe pump.

EXAMPLE 2

Surface Decorating Process of Inner Wall of Microchannel

In the case of a microchip made of glass or quartz, to prevent nucleic acid from adhering to the surface of an inner wall of a microchannel, surface hydroxyl groups on the inner wall of the microchannel need to be coated. To coat the surface hydroxyl groups, a surface decorating process by a silane coupling agent having a reaction group with an alkyl group has been widely employed. Accordingly, in the inner wall process of the microchannel, the surface decorating process may be performed by using the silane coupling agent. However, octadecyltrichlorosilane that is ordinarily used has three chlorine groups as reaction groups for decorating the surface and not only reacts with the surface hydroxyl groups on the inner wall of the microchannel, but also forms a polymer by the polymerization of molecules. Accordingly, the molecules of octadecyltrichlorosilane react with each other to form a polymer so that dust is generated. The dust generated in the surface decorating process of not the microchannel, but a flat substrate such as a slide glass can be washed away by a solvent without generating a problem. However, the dust generated in the process of the inner wall of the microchannel cannot be easily washed out. When a check structure is provided in the microchannel, the dust can be especially hardly removed. The dust remaining in the microchannel not only becomes an obstacle for transporting liquid or beads in the microchannel, but also causes a trouble in an adsorbing process of nucleic acid. Further, dichlorodimethylsilane having two chlorine groups as reaction groups has been also widely employed. However, dichlorodimethylsilane has a low boiling point (70° C.) and a high volatility, so that its safety is low. Further, since the dichlorodimethylsilane has the two reaction groups, the production of polymers due to the polymerization of the molecules cannot be completely prevented.

Thus, a surface decorating agent was examined in which a single reaction group was included, the polymers were not produced in principle, the boiling point was high and the volatility was low with a high safety, and the liquid could be easily treated at ordinary temperature. For instance, triethylchlorosilane has one chlorine group as a part of a reaction group and does not produce a polymer in principle. In addition thereto, since triethylchlorosilane has a boiling point of 145° C. and a melting point of −50° C., the triethylchlorosilane has the low volatility at ordinary temperature. Further, since the triethylchlorosilane is liquid, the triethylchlorosilane is readily diluted with a solvent such as toluene and easily treated.

The surface decorating process of the inner wall of the microchannel was carried out by using the triethylchlorosilane or the octadecyltrichlorosilane. Dehydrate toluene was used as a solvent to prepare 5% solutions of them respectively. Both the solutions were compared with each other by using the experimental system described in the Example 1. The prepared solution was injected to the liquid reservoir and sucked by the syringe pump to inject the solution to the microchannel. A flow rate was set to 10 μl per minute and the solution of 50 μl was injected to carry out a surface decoration. Then, the dehydrate toluene of 50 μl or more was injected to wash the microchannel after a surface treatment. The microchannel during a washing operation was observed by an optical microscope. In the octadecyltrichlorosilane, the dust was produced in the microchannel, however, the dust was not produced in the triethylchlorosilane. In the triethylchlorosilane, a concentration was further raised to 10% and the same process was tried. Then, the dust was not produced.

EXAMPLE 3

Extraction of Nucleic Acid in Microchannel

Figure 5:
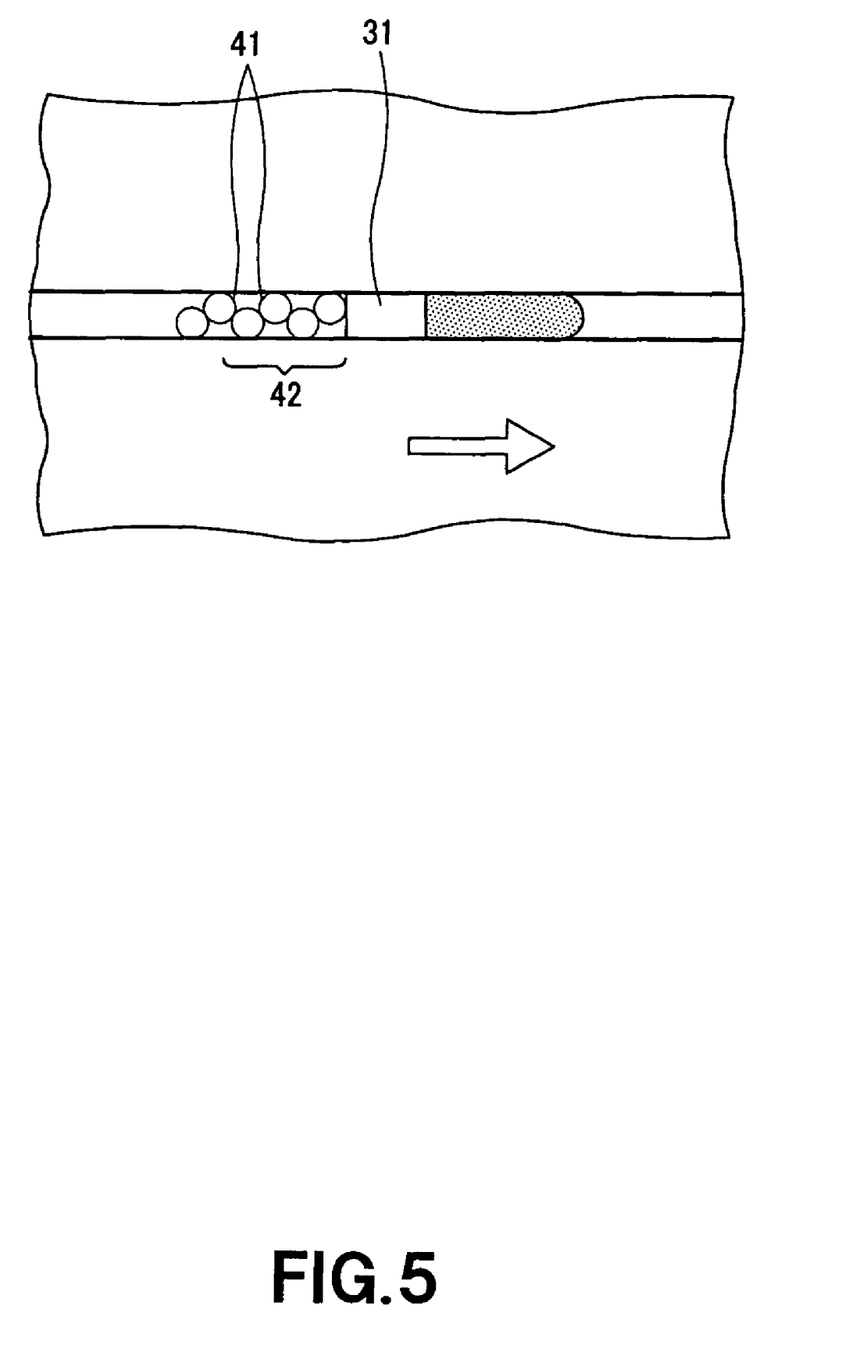
FIG. 5 is a schematic view of an optical microscopic photograph illustrating the adsorption of DNA as an embodiment.

The experimental system described in the Example 1 was used to try to adsorb nucleic acid. The surface of the inner wall of a microchannel was treated by using 10% triethylchlorosilane in the same manner as described in the Example 2. ColE1 DNA was used as the nucleic acid. Saturated sodium iodide solution was used chaotropic ion solution. The microbeads of 0.2 g described in the Example 1 was suspended in the sodium iodide solution in the ratio of 1 1. The obtained solution of 25 μl was injected to the microchannel from a liquid reservoir to form a column. As a solvent, sodium iodide was used to prepare 1% DNA solution and the DNA solution was injected to the microchannel from the liquid reservoir. Then, SYBRGreen I solution as a fluorescent dye of the DNA was injected to the microchannel from the liquid reservoir. When the microchannel was observed by an optical microscope, it was recognized that only the column part 42 of the silica microbeads 41 emitted fluorescence as shown in FIG. 5. It was recognized that the DNA was adsorbed by the silica microbeads 41 used in the Example 1. The fluorescence was not found in the microchannel except the column part 42 and it was recognized that the DNA was not adsorbed on the surface of the inner wall of the microchannel.

The adsorption and desorption of the nucleic acid were examined by using the experimental system described in the Example 1. The experimental system was the same as described above. The microbeads described in the Example 1 were injected to the microchannel to form the column, and then, the nucleic acid was injected. As the nucleic acid, Lambda DNA was used. The adsorption of the Lambda DNA to the microbeads was recognized by using the optical microscope. Hot pure water at 60° C. or higher was prepared and injected to the microchannel from the liquid reservoir. Then, the desorption of the Lambda DNA from the microbeads was recognized.

As described above, since the adsorption and desorption of the nucleic acid to/from the microbeads were recognized, it was found that the extraction of the nucleic acid could be realized in the microchannel.

It is to be understood by a person with ordinary skill in the art that the present invention is not limited to the above-described embodiments and Examples described by referring to the drawings, and various changes, substitutions or equivalence thereto may be made without departing the attached claims and the gist thereof.

INDUSTRIAL APPLICABILITY

As described above in detail, according to the present invention, a new technical means can be provided that can be produced and prepared at low cost as a microchip technique using microbeads that are not only effective for extracting nucleic acid, but also useful as various kinds of reaction carriers, and in which the generation of stagnation in the flow of a liquid sample can be suppressed, the microbeads can be smoothly and simply injected, filled and transported and the generation of dust can be also suppressed. Further, a new extracting method for nucleic acid using the new technical means can be provided.

The invention claimed is:

1. A microchip for extracting nucleic acids, the microchip comprising:
a first substrate; and
a second substrate connected with the first substrate to define a connecting surface therebetween, the first substrate and the second substrate defining a microchannel in the connecting surface by a first groove part of the first substrate and a second groove part of the second substrate, the first groove part having a first protruding part and the second groove part having a second protruding part,
wherein one of the first and second substrates includes a first inlet and a second inlet connected to the microchannel, the first inlet having received therein a first liquid containing microbeads, the second inlet having received therein a second liquid containing nucleic acid,
wherein the microchannel includes a gap part formed by the first protruding part and the second protruding part, the gap part having a sectional size variable by a movable protruding part in the first groove part or in the second groove part, the movable protruding part being the first protruding part or the second protruding part, wherein, when the microchip is in use, the gap part is configured to block microbeads of a size greater than the sectional size of the gap part, and
wherein the microchannel has an inner wall surface treated with triethylchlorosilane.

2. The microchip according to claim 1, wherein the first protruding part is opposed to the second protruding part.

3. The microchip according to claim 1, wherein the gap part is formed by inserting the first protruding part in the second groove part or by inserting the second protruding part in the first groove part.

4. The microchip of claim 1, wherein the first and second substrates comprise glass or quartz.

5. The microchip of claim 4, wherein the substrates consist essentially of glass or quartz.

6. A kit for extracting nucleic acid, including:
the microchip according to claim 1, wherein
the microbeads introduced into the microchannel of the microchip have surface hydroxyl groups.

7. The kit for extracting nucleic acid according to claim 6, wherein the microbeads include at least one of silica microbeads having a diameter of 10 μm or smaller, hollow silica microbeads, and resin microbeads.

8. The kit for extracting nucleic acid according to claim 6, wherein the surface hydroxyl groups are coated with a coupling agent.

9. The kit for extracting nucleic acid according to claim 8, wherein the coupling agent includes a silane coupling agent including trialkyl halogenosilane as a main component.

10. A method for extracting nucleic acid using the kit according to claim 6, wherein the nucleic acid to be processed is adsorbed on surfaces of the microbeads received in the microchannel of the microchip.

11. The method according to claim 10, wherein the nucleic acid is adsorbed on the surfaces of the microbeads under the existence of chaotropic ions.

* * * * *